United States Patent [19]
Allaire et al.

[11] Patent Number: 5,040,419
[45] Date of Patent: Aug. 20, 1991

[54] METHODS AND APPARATUS FOR NON-DESTRUCTIVE TESTING OF MATERIALS USING LONGITUDINAL COMPRESSION WAVES

[75] Inventors: Claude Allaire, Chicoutimi-Nord; Lionel Talbot, deceased, late of Ville de la Baie, both of Canada, by Mariette Talbot, executrix

[73] Assignee: Alcan International Limited, Montreal, Canada

[21] Appl. No.: 467,654

[22] Filed: Jan. 19, 1990

[51] Int. Cl.⁵ ............................................. G01N 29/00
[52] U.S. Cl. ..................................................... 73/597
[58] Field of Search ................ 73/597, 596, 644, 579, 73/589

[56] References Cited
U.S. PATENT DOCUMENTS

| | | | |
|---|---|---|---|
| 4,297,884 | 11/1981 | Leveque et al. | 73/579 |
| 4,872,344 | 10/1989 | Grebenkin et al. | 73/579 |

FOREIGN PATENT DOCUMENTS

2069697 8/1981 United Kingdom .................. 73/589

Primary Examiner—Hezron E. Williams
Assistant Examiner—Louis M. Arana
Attorney, Agent, or Firm—Cooper & Dunham

[57] ABSTRACT

The non-destructive testing of materials, particularly coarse grain materials such as the carbonaceous materials used in the anodes and cathodes of an aluminium smelting furnace, using longitudinal compression waves employs a waveguide to apply the waves to a specimen, the and specimen having a cross-sectional dimension Dg of between 3 and 5 times the material average grain size Dg. Alternatively, or in addition, the waves used preferably are of effective wavelength from about 30Ds to 50Ds. Alternatively, or in addition, the effective wavelength of the waves is preferred to be approximately equal to the length of the sample; the necessary very long samples may be obtained by connecting a plurality of smaller elementary samples end-to-end. The apparatus may include a controllable furnace for cycling the sample to determine the change with temperature of the physical characteristic that is being measured. The methods and apparatus employ relatively low frequencies, in the sonic range, and high powers; although particularly suited for measurements with coarse grain materials they are also very effective with more usual fine grain materials, such as ceramics.

44 Claims, 3 Drawing Sheets

METHODS AND APPARATUS FOR NON-DESTRUCTIVE TESTING OF MATERIALS USING LONGITUDINAL COMPRESSION WAVES

FIELD OF THE INVENTION

This invention is concerned with improvements in and relating to methods and apparatus for the non-destructive testing of materials using longitudinal compression waves in the sonic and ultrasonic ranges.

REVIEW OF THE PRIOR ART

The use of longitudinal compression waves for the non-destructive testing of materials is now a mature art, particularly the use of such waves in the ultrasonic range of frequencies. In addition to testing bodies of material for the presence of cracks, holes and other flaws they are now used to determine various physical characteristics of the materials, such as Poisson's Ratio, porosity and density, and its elastic constants, including the axial modulus of elasticity and the changes in such modulus with temperature. The equipment currently in use employs pulses of high frequency waves, i.e. in the range from about 100 kiloHertz to one or two mega-Hertz, because of their relative ease of generation and the low powers that can be employed. Such apparatus is very successful when used with small samples of fine grain materials, such as metals and fine grain ceramics, but is not as succesful when attempts are made to employ them with relatively large samples of relatively coarse grain materials.

Examples of coarse grain materials whose axial modulus of elasticity must be tested are the refractory materials employed in the manufacture of bricks and castables as used in many industries, including the aluminium industry. Such materials are exposed in service to thermal shock conditions whose effect on the materials, in particular their degradation, is related to this modulus. Another specific example of coarse-grain materials where the axial modulus of elasticity must be tested is those used in the carbon based anodes and cathodes that are employed in the production of aluminium; these electrodes are consumed during the process and must be replaced regularly. The conditions under which they operate are very onerous, involving their exposure to operating temperatures of about 1000° C. The too-rapid consumption or mechanical failure of an electrode can markedly increase the cost of operation and reduce the output of the reduction cell in which it is installed, and prior testing of the electrodes, as well as samples of the materials from which they are made, is essential in order to ensure that they meet minimum standards. Attempts to obtain meaningful results with the equipment currently available have not been satisfactory.

DEFINITION OF THE INVENTION

It is therefore a principal object of the invention to provide new methods and apparatus for the non-destructive testing of materials using longitudinal compression waves, such methods being particularly suited to the testing of relatively coarse grain materials and/or large samples thereof.

It is another object to provide such methods and apparatus that, while particularly suited to the testing of coarse grain materials and/or large samples thereof, is nevertheless also satisfactory for use in the testing of finer grain materials and/or smaller samples.

In accordance with the present invention there is provided a method of non-destructive testing of coarse grain materials using longitudinal compression waves including the steps of:

determining the average grain size $D_g$ of the material of the sample;

preparing a sample of the material with two sample parallel faces having a cross-sectional dimension of at least $D_s$, where $D_s$ is from about $3 D_g$ to about $5 D_g$;

applying to one of the sample parallel faces a waveguide for transmission to the sample of longitudinal compression waves from a source thereof, the waveguide having a cross-sectional dimension at least at the sample parallel face to which it is applied of $D_w$ for which its acoustic impedance is between about 0.5 and about 2 times that of the sample material;

applying the longitudinal compression waves to the sample through the waveguide; and testing the material by measuring their propagation characteristics through the sample.

Preferably the value of $D_s$ is $4 D_g$.

Also in accordance with the invention there is provided a method of non-destructive testing of materials using longitudinal compression waves including;

preparing a sample of the material with two sample parallel faces having a cross-sectional dimension of at least $D_s$;

applying to one of the sample parallel faces a waveguide for transmission to the sample of longitudinal compression waves from a source thereof, the waveguide having a cross-sectional dimension $D_w$ at least at the sample parallel face to which it is applied for which its acoustic impedance is between about 0.5 and about 2 times that of the sample material; and applying to the sample through the waveguide longitudinal compression waves of effective wavelength from $30 D_s$ to $60 D_s$; and testing the material by measuring their propagation characteristics through the sample.

Preferably the effective wavelength of the longitudinal compression waves is from $30 D_s$ to $50 D_s$.

Further in accordance with the invention there is provided a method of non-destructive testing of coarse grain materials using longitudinal compression waves including:

preparing a sample of the material having two parallel end faces;

applying to one of the sample end faces a waveguide for the transmission to the sample of the longitudinal compression waves from a source thereof;

applying to the sample through the waveguide longitudinal compression waves of effective wavelength between 0.5 and 1 times the length of the sample; and testing the material by measuring their propagation characteristics through the sample.

Preferably the effective wavelength is one times the length of the sample.

Further in accordance with the invention there is provided a method of non-destructive testing of coarse grain materials using longitudinal compression waves including:

preparing a plurality of elementary samples of the coarse grain material, each having two parallel elementary sample end faces;

mounting the elementary samples end face to end face with the immediately adjacent end faces butting to be in close physical contact with one another and to form a single composite sample with two composite sample parallel end faces;

applying to one of the composite sample end faces a waveguide for the transmission to the sample of the longitudinal compression waves from a source thereof;

applying to the composite sample through the waveguide longitudinal compression waves of effective wavelength between 0.5 and 1 times the length of the composite sample; and testing the material by measuring their propagation characteristics through the sample.

Preferably the effective wavelength is one times the length of the sample.

Further in accordance with the invention there is provided apparatus for the non-destructive testing of coarse grain materials using longitudinal compression waves and with a sample of the material of known average grain size Dg and having two parallel faces of cross-sectional dimension of at least Ds, where Ds is from about 3 Dg to about 5 Dg, the apparatus comprising:

a waveguide for application to one of the sample parallel faces for the supply to the sample of the longitudinal compression waves;

wherein the cross-sectional dimension Dw of the waveguide at least at the sample parallel face to which it is applied is a value for which its acoustic impedance is between about 0.5 and about 2 times that of the sample material;

longitudinal compression wave generating means connected to the waveguide for supplying longitudinal compression waves thereto;

longitudinal compression wave detection means connected to the sample to receive such waves therefrom; and measuring means connected to the wave generating means and the wave testing means and for testing the sample by measuring the propagation characteristics of the longitudinal compression waves through the sample.

Preferably the value of Ds is 4 Dg.

Further in accordance with the invention there is provided apparatus for the non-destructive testing of materials using longitudinal compression waves and with a sample of the material having two parallel faces having a cross-sectional dimension of at least Ds, the apparatus comprising:

a waveguide for application to one of the sample parallel faces for the supply to the sample of longitudinal compression waves;

wherein the waveguide at least at the sample parallel face has a cross-sectional dimension Dw for which its acoustic impedance is between about 0.5 and about 2 times that of the sample material;

longitudinal compression wave generating means connected to the waveguide for supplying longitudinal compression waves thereto, the wave generating means generating waves of effective wavelength from about 20 Ds to about 60 Ds;

longitudinal compression wave detection means connected to the sample to receive such waves therefrom; and measuring means connected to the wave generating means and the wave testing means and for testing the sample by measuring the propagation characteristics of the longitudinal compression waves through the sample.

Preferably the effective wavelength of the longitudinal compression waves is from 30 Ds to 50 Ds.

Further in accordance with the invention there is provided apparatus for the non-destructive testing of materials using longitudinal compression waves and for use with a sample of the material having two parallel faces, the apparatus comprising:

a waveguide for the application to one of the sample parallel faces for the supply to the sample of longitudinal compression waves;

longitudinal compression wave generating means connected to the waveguide for supplying longitudinal compression waves thereto;

wherein the effective wavelength of the longitudinal compression waves is between 0.5 and 1 times the length of the sample to be employed with the apparatus;

longitudinal compression wave detection means connected to the sample to receive such waves therefrom; and measuring means connected to the wave generating means and the wave testing means and for testing the sample by measuring the propagation characteristics of the longitudinal compression waves through the sample.

Preferably the effective wavelength is one times the length of the sample.

BRIEF DESCRIPTION OF THE DRAWINGS

Methods and apparatus that are preferred embodiments of the invention will now be described, by way of example, with reference to the accompanying drawings, wherein.

DESCRIPTION OF THE PREFERRED EMBODIMENTS

The methods and apparatus of the invention were developed for the measurement of the physical properties of refractory and carbon materials, the latter being employed to make both the anodes and the cathode in a typical aluminium smelting furnace. Such a furnace consists of a bath of heat-resistant material, usually measuring at least about 5 meters (16 feet) by 3 meters (10 feet), lined with a bath-shaped carbon based cathode of thickness about 46 cm (18 ins). The cathode contains a pool of molten aluminium, which has been obtained by reduction from an electrolyte consisting of alumina in a solvent therefor, usually cryolite, the layer of elctrolyte overlying the molten aluminium and being kept for the operation of the process at a temperature of about 1000° C. (1832° F.). A plurality of prebaked carbon-based anodes, usually a minimum of about eighteen, which when new measure a minimum of about 61 cm (24 ins) in height about 51 cm (20 ins) in width, and about 82 cm (32 ins.) in length, extend downward into the bath from a overhead combined current supplying bus-bar and support structure that permits the anodes to be lowered into the pool as they are consumed during the smelting process. The cathode is also consumed, but much more slowly, and it will be apparent that both cathode and anodes are subjected to extremely arduous conditions that are highly likely to lead to mechanical failure if the carbon materials do not meet critical standards as to freedom from flaws, appropriate axial moduli of elasticity, and predictable changes in such modulus with changes in electrode temperature from ambient up to the maximum temperature of the process.

The axial modulus of elasticity is one of the physical characteristics of a material that can be determined by applying pulses of longitudinal compression waves to a sample and measuring the wave velocity through it, either by measuring the transit time of a pulse through the specimen, or the transit time between two successive echoes obtained from opposite parallel ends thereof. With the echo method the value is calculated using the equations:

$$V_L = \frac{2L}{R - Q} \text{ and } E = D \cdot V_L^2$$

where $V_L$ = wave speed in longitudinal mode;
L = length of sample;
R = transit time;
Q = a correction factor;
E = axial modulus of elasticity; and
D = density of material The relation required for calculation with the direct transit method is given below. Attempts to use the testing apparatus currently available with such materials have proven to be unsuccessful in that they only permit the testing of relatively small samples having a maximum cross-sectional dimension in the range of the average coarse grain size of the carbon electrode material. For the purpose of this application coarse grain materials are those which are retained by a No. 10 Tyler Screen (U.S. No. 12—Sieve opening 1.68 mm).

Figure 1:
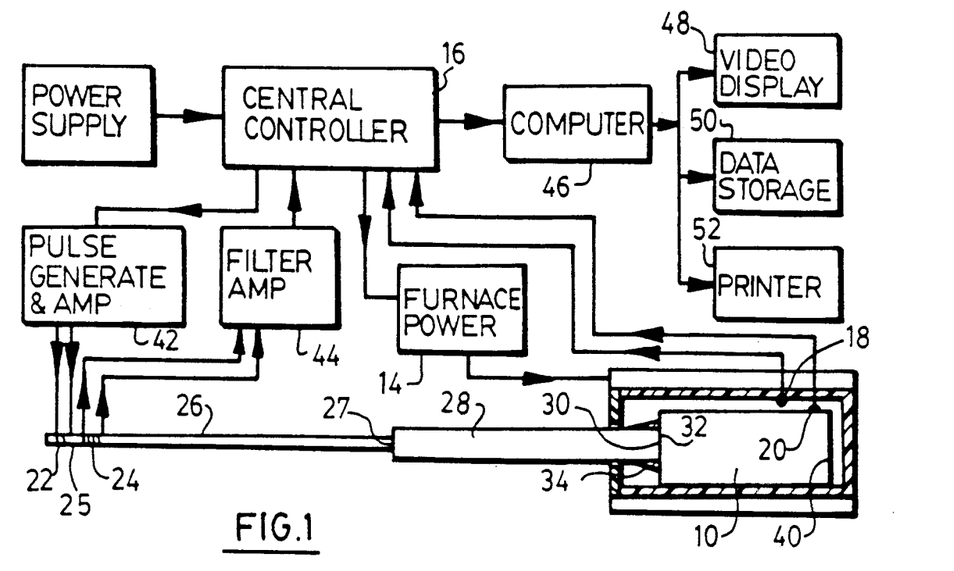
FIG. 1 is a illustrative view of a first embodiment employing the detection and measurement of pulse echoes reflected back through the sample.
Figure 2:
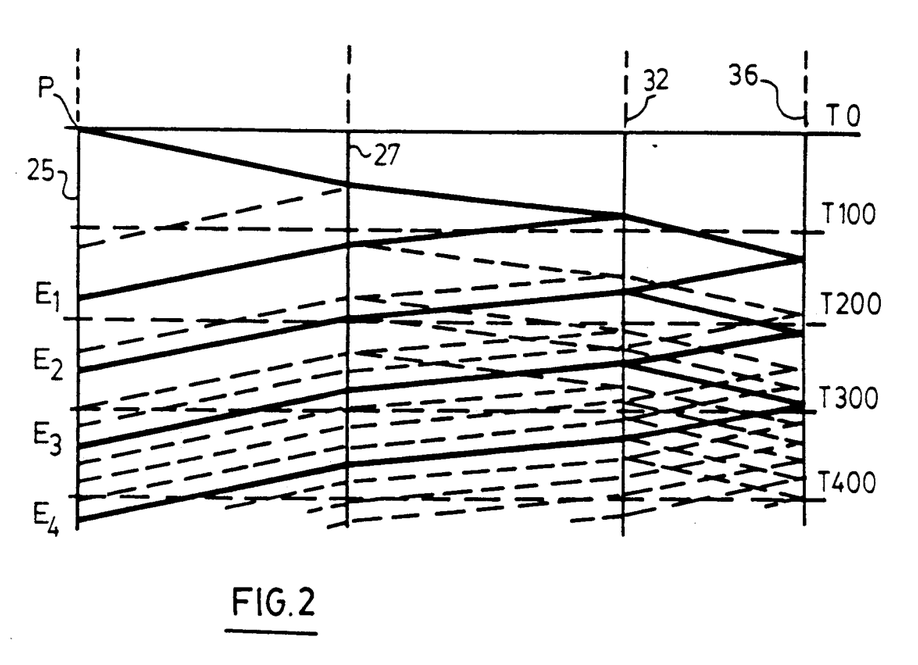
FIG. 2 is a diagram correlated in longitudinal dimension along the horizontal axis with the apparatus of FIG. 1, and along the vertical axis with elapsed time from the moment of generation of an initial pulse, the paths of the initial pulse and significant echoes thereof being shown in solid lines, while all other echo paths are shown in broken lines.

Referring now to FIGS. 1 and 2, a sample 10 to be tested is mounted in a furnace 12 supplied with heating current from a power source 14 under the control of a central controller 16 that monitors the furnace temperature via thermometer 18 and the sample temperature via thermometer 20. The other functions of the controller 16 will be described below. A pulse transmitting transducer 22 and a pulse receiving transducer 24 are mounted together at one end 25 of a tungsten waveguide 26, the other end 27 of which is connected to an alumina waveguide 28 protruding into the furnace 12. An alumina waveguide is used if the furnace temperature for the test is about 1000°–1200° C., or higher, and/or the test is carried out under an oxidising atmosphere, under which conditions the good acoustic properties and physical integrity of a tungsten waveguide would tend to be lost. Such a waveguide would be required therefore in the testing, for example, of the refactory bricks that are used in the carbon baking furnaces of the aluminium industry, in which furnaces the bricks can be exposed to temperatures of about 1300°–1350° C. The end 30 of the alumina waveguide adjacent the sample is connected to the adjacent sample face 32 by a carbon glue 34 that also ensures efficient transfer of the longitudinal waves from the waveguide into the sample. The choice of a suitable glue and the glueing techniques to be employed are known to those skilled in the art and need not further be described herein. The end surface 30 of the waveguide and the end surfaces, 32 and 40 of the sample are made parallel to one another to reduce spurious signals as much as possible.

Pulses of the required amplitude, duration and pulse frequency, each pulse consisting of a number of waves or oscillations of the required frequency, are generated under control of the controller 16 by pulse generator and amplifier 42 and fed to transmitting transducer 22, while the echo pulses received by receiving transducer 24 are fed to a signal filter and amplifier 44. The echo pulse signals produced by circuit 44 are fed to controller 16 and thence to computer 46 which computes the physical characteristic under test, employing suitable software and set point values that have previously been determined. The values obtained together with other necessary identifying and correlated data are fed by the computer to a video display 48, a data storage system 50 and a printer 52.

As will be seen from FIG. 2 a pulse P generated at time $T_0$ is propagated through the waveguide 26 at a corresponding speed which changes at junction 27 as the pulse enters the waveguide 28, and changes again at the junction 32 as the pulse enters the sample 10. The first echo $E_1$ of practical interest is that received by the transducer 24 from the junction 32, while the second echo $E_2$ of interest is that received from the end face 36, which has passed twice through the specimen. The time intervals shown are in microseconds. Subsequent echoes of interest $E_3$ and $E_4$ are those which have been the subject of internal reflection within the sample itself between the surfaces 32 and 36. The time intervals between the successive echoes $E_2$, $E_3$, $E_4$ etc. should be substantially equal and their measurement and averaging can therefore be used to more accurately determine the value for the sample under test.

Before a series of tests are conducted one or several test runs are normally effected in order to verify the test set-up and to obtain necessary set points. At this time the gross relative positions of the desired echoes $E_1$, $E_2$ etc. or transmitted signals $T_1$, $T_2$ etc. are determined and noted, so that subsequent measurements can be made more precisely.

It is preferred to operate the apparatus with waves that are as much as possible purely longitudinal mode, and this requires that their effective wavelength is at least 8 to 10 times the minimum cross-sectional dimension $D_C$ of each component through which the waves pass, i.e. the two waveguides 26 and 28 and the sample, the frequency of the waves remaining the same in all of the components. We have found that for successful measurement with coarse grain materials the sample parallel face 32 that is contacted by the waveguide 28 should be of a minimum transverse cross-sectional dimension $D_S$ at its interface, which dimension is correlated with the average coarse grain size $D_g$ of the sample material. In the case of a face that is circular the dimension $D_S$ will be its diameter, and for a square cross-section face will be the length of one side, these being the two sections that generally are used. The value of $D_S$ should be a minimum of 3 times $D_g$, and can be as much as 5 times $D_g$; preferably it is 4 $D_g$ (the mean coarse grain size of the carbon material of aluminium smelting anodes generally averages 1.26 cm (0.5 in)). In the preferred embodiment described above the value of Ds is about 5 cm (2 ins.).

The waveguides will usually be of circular cross-section to avoid as much as possible the generation of alternative modes of propagation, and their dimension Dw, which will therefore be the diameters, should be such that the acoustic impedance Z, at least at the sample parallel face to which it is applied, is more than about 0.5 and less than about 2 of that of the sample to achieve an adequate ratio between transmission through the sample and reflection from the interface. In practice a minimum of 65% transmission and a maximum of 35% reflection is desired. The acoustic impedance Z in Kg/sec is defined by the relation:

$$Z = DVS$$

where

D = Density of material in Kg/m$^3$
V = Mean wave velocity in m/sec
S = Transverse cross-sectional area of the waveguide or the sample in m$^2$.

It is now found that by this action the coupling between the waveguide and the material of the sample is increased to the extent that meaningful results can be obtained.

To obtain minimum reflection of the waves at the interface between the waveguides 26 and 28 their diameters should be such that, at least where they contact each other, their respective acoustic impedances do not differ by more than about 10%-15%. If this is not possible the two waveguides should be coupled by an impedance matching component that is interposed between them and glued to the adjacent ends. By way example a particularily suitable component is made of aluminium of length equal to one quarter of the wavelength of the waves in it, and of circular cross-section; the component is provided at both ends with respective parallel faces of diameters such that its acoustic impedance at those locations is equal to that of the waveguides to which it is connected.

The dimensions, etc. for this specific embodiment are as follows:

|  | Waveguide 26 | Waveguide 28 | Sample 10 |
| --- | --- | --- | --- |
| Material | Tungsten | Alumina | Refractory |
| Mean Velocity V (m/sec.) | 5,000 | 10,000 | 3,000 |
| Length, L (cm) | 60 | 60 | 50 |
| Diameter, D$_C$ (cm) | 0.30 | 0.50 | 1.5 |
| Z (kg/sec.) | 702 | 777 | 1,380 |

Another factor that can be employed to lead to improved results with these coarse grain materials is the use of longitudinal waves of wavelength that are also correlated with the transverse cross-sectional dimension Ds of the sample. Thus, this wavelength should be between from about 20Ds to about 60 Ds, and preferably it is between the values 30 Ds and 50 Ds.

In this embodiment the samples are of square transverse cross-section of 1.5 cm side length (Ds); the wavelength of the waves is 10 Ds so the output frequency of transducer 22 is 20 KHz, which is very low by current standards for such equipment. The refractory materials used in this example have a coarse grain size of 0.30–0.40 cm, and the mean velocity in the material is about 3000 cm/sec. If the materials are of larger means grain size or the mean velocity is lower, then the transverse cross-section dimension Ds of the sample and its length should be increased proportionally and the frequency should be reduced proportionally.

The preferred range of wavelengths used in the methods and apparatus of this invention is about 1 KHz to 50 KHz, and in general it is preferred that the frequency be kept at a value of 20 KHz or lower. Such low frequencies and the relatively high power that is needed (e.g. from about 25 to about 35 watts) virtually dictates the use of magnetostrictive generators for the pulse producing means 22. Piezoelectric detectors 24 are preferred.

Yet another factor that can be employed to give improved results, by increasing the ease and/or the precision of detection of the signals of interest, is the use of a specimen whose length is correlated with the effective wavelength of the waves applied to it, or vice versa. This has, in particular, the advantage that resonance is produced because of the correlation of sample length and wavelength, resulting in a substantial increase in the amplitudes of the echoes obtained, increasing the signal/noise ratio and enabling good results to be obtained, especially when the subsequent echoes $E_2$-$E_n$ are detected and employed in the determination.

A pulse train signal is always used and will usually consist of a plurality of damped waves within the pulse envelope, so that its effective wavelength will be the number of cycles in the train times the wavelength of each wave. The effective wavelength of the pulse train applied to the sample should be between 0.5 and 1 times the length of the sample, and approximately an integral fraction 2/X of the length, where X is a whole number integer. Preferably it is approximately equal to the length of the sample. With the specific embodiment already described a pulse train of only a single wave requires a sample length of about 15 cm (5.9 ins.). It is however more usual for the pulse train to consist of from about 3 to 5 damped waves, for a required sample length of from about 45 cm (118 ins.) to about 75 cm (29.5 ins.).

Figure 3:
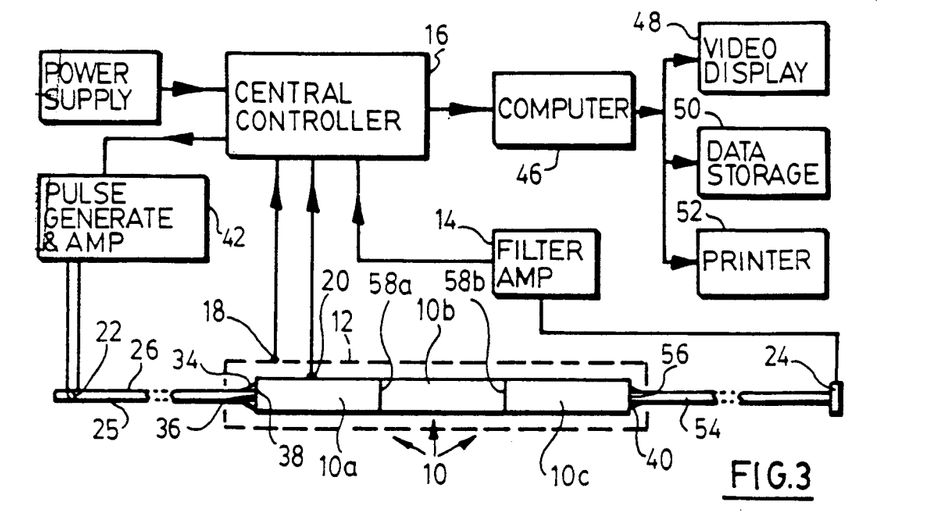
FIG. 3 is an illustrative view similar to FIG. 1 of a second embodiment employing the detection and measurement of pulses transmitted through the sample.
Figure 4:
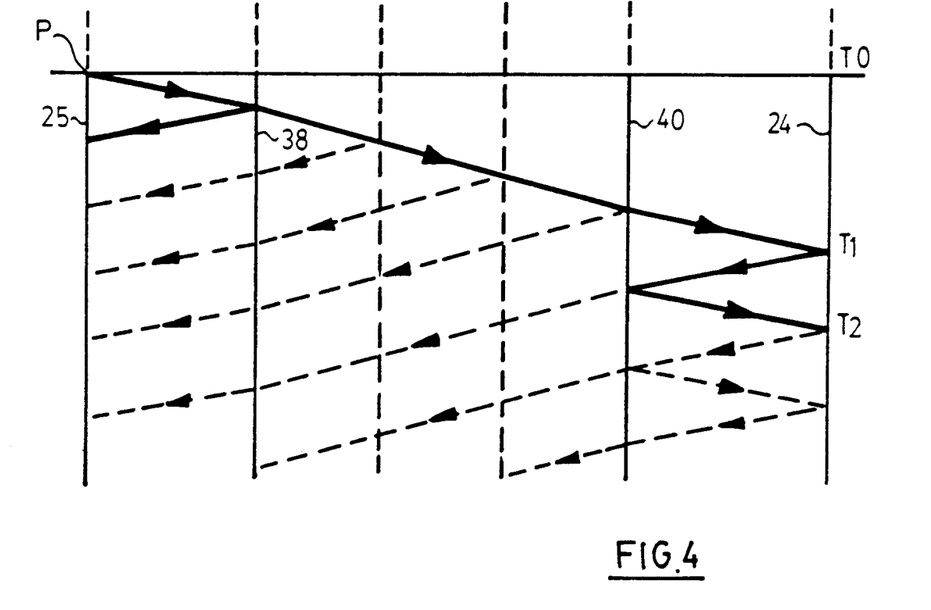
FIG. 4 is a diagram similar to FIG. 2 correlated with the apparatus of FIG. 3.

FIGS. 3 and 4 illustrate an apparatus of the invention in which the axial modulus of elasticity, is determined by measurement of the transmission of the pulse train through the sample. The same reference numbers as were used in FIG. 1 are used wherever possible. The furnace 12 is indicated only diagrammatically and its power source is not shown. The tungsten waveguide 26 is connected directly to the adjacent face 38 of the sample so that the two parallel faces 36 and 38 at the interface but one another. The other end face 40 of the sample has another tungsten waveguide 54 of the same length as the waveguide 26 connected thereto so that the two faces 40 and 56 also but one another, the pulse receiving transducer 24, which is of piezoelectric type, being mounted at the end of the waveguide 54.

It is also preferred with such apparatus to operate with the compression wave propagated in the first longitudinal mode. In order to obtain satisfactory results the wavelength of the wave applied to the sample is about 10 times its cross-section dimension Ds, while the waves travelling in the waveguides should have a wavelength which is at least ten times their diameter. In this specific embodiment this dimension Ds of the sample is 3 cm (1.2 in.), so that the wavelength is about 30 cm (11.8 in.) corresponding to a frequency of about 8 KHz. The length of the sample should be correlated with the effective wavelength of the wave applied to it, or vice versa, as described above, so that the received signal is more easily detectable and does not interfere with the other modulations contained in the pulse train. Ideally the initial pulse could be a single unique wavelength, but in practice the resultant effective pulse wavelength is usually about three to five wavelengths, as described above. This requires therefore a sample whose length is at least 3λ to 5λ, where λ is the actual wavelength in the sample. It will be seen that for the embodiment in question operating with waves of length about 30 cm (11.8 ins.) in the sample, the latter should be 90 to 150 cm (35.4 to 59 ins.) in length, which is difficult if not impossible to achieve, even with such large products as smelting electrodes.

In order to obtain the required length a composite sample 10 is assembled from a plurality of elementary samples, three such elementary samples 10a, 10b and 10c being shown in this embodiment, although two or more than three can also be employed. These elementary samples are produced with parallel end faces and are then glued end face to end face to form the junctions 58a and 58b, etc. until a composite sample of the required length has been obtained. The presence of the junctions in the composite sample considerably increases the number of echoes that are reflected back to the entry waveguide 26 and direct measurement of the waves through the sample is therefore preferred.

Referring also to FIG. 4 the pulse P produced at time $T_0$ produces a first significant signal at time $T_1$ that is detected by the transducer 24. The second significant signal detected by this same transducer at time $T_2$ corresponds to a back and forth propagation of the pulse in the waveguide 54 after its first reflection at the interface of waveguide 54 and transducer 24. The transit time T is related to the difference between successive signals at $T_1$ and $T_2$ and the average axial modulus of elasticity of the string of elementary carbon samples can be determined by the relations:

$$T = T_1 - (T_2 - T_1) = 2T_1 - T_2$$

and $$E = D(L/T)^2$$

where
E = Axial modulus of elasticity
T = Transit time
D = Density of material
L = Length of sample The dimensions, etc. for the specific example of FIG. 3 are as follows:

| | Waveguide 26 | Sample 10 | Waveguide 54 |
|---|---|---|---|
| Material | Tungsten | Carbon | Tungsten |
| Mean Velocity, V (m/sec.) | 5,000 | 2,500 | 5,000 |
| Length, L (cm) | 100 | 150 | 100 |
| Diameter, D (cm) | 0.792 | 3 | 0.792 |
| Z (kg/sec.) | 4930 | 3460 | 4930 |

In this embodiment the samples are of square transverse cross-section of 3 cm side length; the frequency of transducer 22 is about 8 KHz. Both carbon and refractory materials are non-homogenous solids and this aspect of the invention provides the possibility of increasing the number of elementary samples and performing a statistical evaluation of all of them in a single test; this is a substantial advantage in that the assembled electrode is composed of a number of blocks and such a test is quite representative of the conditions encountered in commercial application. Also it is not practical to cut single samples of the necessary length, which it will be seen in this embodiment is 150 cm (59 ins.); it is much more practical to cut three samples of 50 cm (19.7 ins.) each long, and even more practical to cut five samples of 30 cm (11.8 ins.) length. It is entirely practical therefore with the methods and apparatus of the invention to operate with samples measuring about 5 cm (2 ins.) in transverse dimension and about 150 cm (59 ins.) in length.

Although with the invention it is preferred to operate with frequencies in the sonic range of 1 kHz to 20 kHz, it is nevertheless possible to employ frequencies in the ultrasonic range from 20 kHz to 2.5 MHz and still obtain the improved results of the invention. Moreover, although the invention is particularly described in this application to measurements with coarse-grain materials, nevertheless it is also utilizable in measurements on fine grain materials, even though the reverse is not true for existing apparatus as used for fine grain materials. This permits the testing of most of the more usual refactory and carbon materials whose average coarse grain size Dg generally falls in the range of 1 cm and less.

Figure 5:
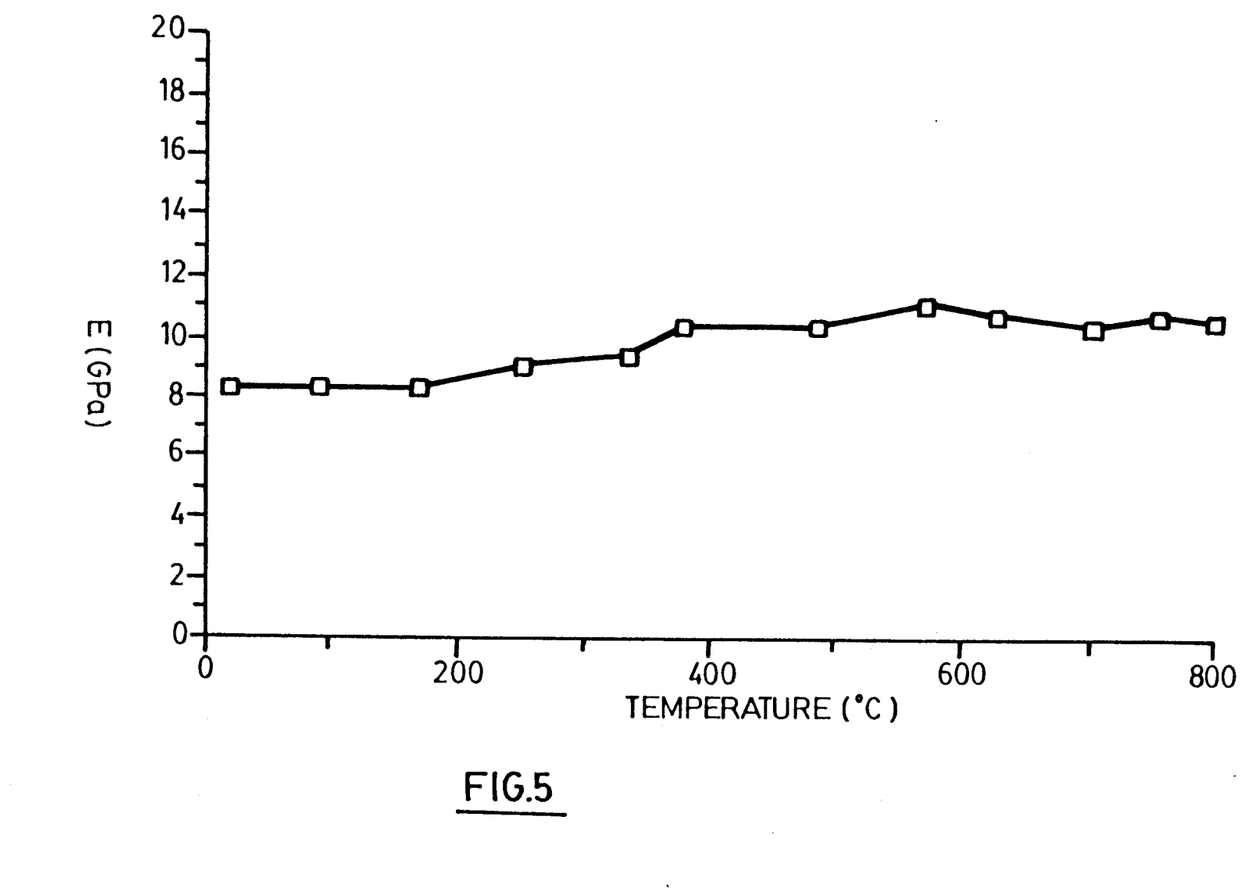
FIG. 5 is a graph showing a typical plot obtained with methods and apparatus of the invention during the measurement of the axial modulus of elasticity of a sample exposed to an increasing temperature.

The variation with temperature in any of the physical constants that are being measured is readily determined by supplying pulses continuously and at a fixed repetition rate to the sample while the computer 46 continuously calculates the characteristic under test. The furnace control is operated at the same time to take the sample through a heat treatment cycle involving its progressive heating to a maximum temperature, maintainance of the temperature at this value for a period, and then cooling back to a lower temperature. A typical graph of the variation obtained with rising temperature during heating is shown in FIG. 5. During the initial heating and subsequent cooling portions of the cycle the pulse repetition rate can be much higher than during the high value "plateau" in order to provide increased accuracy during these critical periods. In this example the sample was again of square cross-section of side length 3 cm and measured 150 cm in length. The frequency of the waves was 8 KHZ; the mean longitudinal velocity in the sample was 2500 m/s and the mean elastic modules was 10 GPa.

We claim:

1. A method of non-destructive testing of coarse grain materials using longitudinal compression waves including the steps of:

determining the average grain size Dg of the material of the sample;

preparing a sample of the material with two sample parallel faces having a cross-sectional dimension of at least Ds, where Ds is from about 3 Dg to about 5 Dg;

applying to one of the sample parallel faces a waveguide for transmission to the sample of longitudinal compression waves from a source thereof, the waveguide having a cross-sectional dimension at least at the sample parallel face to which it is applied of Dw for which its acoustic impedance is between about 0.5 and about 2 times that of the sample material;

applying the longitudinal compression waves to the sample through the waveguide; and testing the material by measuring the propagation characteristics of the longitudinal compression waves through the sample.

2. A method as claimed in claim 1, wherein the cross-sectional dimension Ds is about 4 Dg.

3. A method as claimed in claim 1, wherein the longitudinal compression waves applied to the sample are of effective wavelength from 20 Ds to 60 Ds.

4. A method as claimed in claim 3, wherein the effective wavelength of the longitudinal compression waves is from 30 Ds to 50 Ds.

5. A method as claimed in claim 1, wherein the effective wavelength of the longitudinal compression waves is between 0.5 and 1 times the length of the sample.

6. A method as claimed in claim 5, wherein the effective wavelength of the longitudinal compression waves is an integral fraction 2/X of the length of the sample where X is a whole number integer.

7. A method as claimed in claim 5, wherein the effective wavelength of the longitudinal compression waves is at least approximately equal to the length of the sample.

8. A method as claimed in claim 1, including:
preparing a plurality of the said elementary samples of the coarse grain material, each having two parallel elementary sample end faces;
mounting the elementary samples end face to end face with the immediately adjacent end faces butting to be in close physical contact with one another and to form a single composite sample with two composite sample parallel end faces corresponding to the two sample parallel faces of a single sample; and
applying the waveguide to one composite sample end face;
wherein the effective wavelength of the longitudinal compression waves applied to the sample is between 0.5 and 1 times the length of the composite sample.

9. A method as claimed in any claim 8, wherein the effective wavelength of the longitudinal compression waves applied to the sample is at least approximately equal to the length of the composite sample.

10. A method as claimed in claim 1, including the step of cycling the sample through a period of increasing temperature, a subsequent period of high temperature, and a final period of decreasing temperature while the material of the sample is tested.

11. A method of non-destructive testing of materials using longitudinal compression waves including;
preparing a sample of the material with two sample parallel faces having a cross-sectional dimension of value Ds;
applying to one of the sample parallel faces a waveguide for transmission to the sample of longitudinal compression waves from a source thereof, the waveguide having a cross-sectional dimension Dw at least at the sample parallel face to which it is applied for which its acoustic impedance is between about 0.5 and about 2 times that of the sample material; and
applying to the sample through the waveguide longitudinal compression waves of effective wavelength from 20 Ds to 60 Ds; and
testing the material by measuring the propagation characteristics through the sample.

12. A method as claimed in claim 11, wherein the effective wavelength of the longitudinal compression waves is from 30 Ds to 50 Ds.

13. A method as claimed in claim 11, wherein the effective wavelength of the longitudinal compression waves is between 0.5 and 1 times the length of the sample.

14. A method as claimed in claim 13, wherein the effective wavelength of the longitudinal compression waves is an integral fraction 2/X of the length of the sample where X is a whole number integer.

15. A method as claimed in claim 13, wherein the effective wavelength of the longitudinal compression waves is at least approximately equal to the length of the sample.

16. A method as claimed in claim 11, including:
preparing a plurality of elementary samples of the coarse grain material, each having two parallel elementary sample end faces;
mounting the elementary samples end face to end face with the immediately adjacent end faces butting to be in close physical contact with one another and to form a single composite sample with two composite sample parallel end faces; and
applying the waveguide to one composite sample end face;
wherein the effective wavelength of the longitudinal compression waves applied to the sample is between 0.5 and 1 times the length of the composite sample.

17. A method as claimed in claim 16, wherein the effective wavelength of the longitudinal compression waves applied to the sample is at least approximately equal to the length of the composite sample.

18. A method as claimed in claim 11, including the step of cycling the sample through a period of increasing temperature, a subsequent period of high temperature, and a final period of decreasing temperature while the material of the sample is tested.

19. A method of non-destructive testing of coarse grain materials using longitudinal compression waves including:
preparing a sample of the material having two parallel end faces;
applying to one of the sample end faces a waveguide for the transmission to the sample of the longitudinal compression waves from a source thereof;
applying to the sample through the waveguide longitudinal compression waves of effective wavelength between 0.5 and 1 times the length of the sample; and
testing the material by measuring the propagation characteristics of the longitudinal compression waves through the sample.

20. A method as claimed in claim 19, wherein the wavelength is an integral fraction 2/X of the length where X is a whole number integer.

21. A method as claimed in claim 19, wherein the effective wavelength of the waves is at least approximately equal to the length of the sample.

22. A method as claimed in claim 19, including the step of cycling the sample through a period of increasing temperature, a subsequent period of high temperature, and a final period of decreasing temperature while the material of the sample is tested.

23. A method of non-destructive testing of coarse grain materials using longitudinal compression waves including:

preparing a plurality of elementary samples of the coarse grain material, each having two parallel elementary sample end faces;

mounting the elementary samples end face to end face with the immediately adjacent end faces butting to be in close physical contact with one another and to form a single composite sample with two composite sample parallel end faces corresponding to the two sample parallel faces of a single sample;

applying to one of the composite sample end faces a waveguide for the transmission to the sample of the longitudinal compression waves from a source thereof;

applying to the composite sample through the waveguide longitudinal compression waves of effective wavelength between 0.5 and 1 times the length of the composite sample; and testing the material by measuring the propagation characteristics through the sample.

24. A method as claimed in claim 23, wherein the wavelength is an integral fraction 2/X of the length of the sample where X is a whole number integer.

25. A method as claimed in claim 23, wherein the effective wavelength of the longitudinal compression waves is at least approximately equal to the length of the composite sample.

26. A method as claimed in claim 23, including the step of cycling the sample through a period of increasing temperature, a subsequent period of high temperature, and a final period of decreasing temperature while the material of the sample is tested.

27. Apparatus for the non-destructive testing of coarse grain materials using longitudinal compression waves and with a sample of the material of known average grain size $D_g$ and having two parallel faces of cross-sectional dimension of at least $D_s$, where $D_s$ is from about 3 $D_g$ to about 5 $D_g$, the apparatus comprising:

a waveguide for application to one of the sample parallel faces for the supply to the sample of longitudinal compression waves;

wherein the cross-sectional dimension $D_w$ of the waveguide at least at the sample parallel face to which it is applied is a value for which its acoustic impedance is between about 0.5 and about 2 times that of the sample material;

longitudinal compression wave generating means connected to the waveguide for supplying longitudinal compression waves thereto;

longitudinal compression wave detection means connected to the sample to receive such waves therefrom; and measuring means connected to the wave generating means and the wave testing means and for testing the sample by measuring the propagation characteristics of the longitudinal compression waves through the sample.

28. Apparatus as claimed in claim 27, wherein the value of $D_s$ is 4 $D_g$.

29. Apparatus as claimed in claim 27, wherein the longitudinal compression waves applied to the sample are of effective wavelength from about 20 $D_s$ to about 60 $D_s$.

30. Apparatus as claimed in claim 29, wherein the effective wavelength of the longitudinal compression waves is from 30 $D_s$ to 50 $D_s$.

31. Apparatus as claimed in claim 27, wherein the effective wavelength of the longitudinal compression waves is between 0.5 and 1 times the length of the sample to be employed with the apparatus.

32. Apparatus as claimed in claim 31, wherein the effective wavelength of the longitudinal compression waves is an integral fraction 2/X of the length of the sample where X is a whole number integer.

33. Apparatus as claimed in claim 31, wherein the effective wavelength of the longitudinal compression waves is at least approximately equal to the length of the sample to be employed with the apparatus.

34. Apparatus as claimed in claim 31, including:

a furnace in which the sample to be tested can be enclosed; and means for controlling the furnace to cycle the sample through a period of increasing temperature, a subsequent period of high temperature, and a final period of decreasing temperature while the material of the sample is tested.

35. Apparatus for the non-destructive testing of materials using longitudinal compression waves and with a sample of the material having two parallel faces having a cross-sectional dimension of value $D_s$, the apparatus comprising:

a waveguide for application to one of the sample parallel faces for the supply to the sample of longitudinal compression waves;

wherein the waveguide at least at the sample parallel face has a cross-sectional dimension $D_w$ for which its acoustic impedance is between about 0.5 and about 2 times that of the sample material;

longitudinal compression wave generating means connected to the waveguide for supplying longitudinal compression waves thereto, the wave generating means generating waves of effective wavelength from about 20 $D_s$ to about 60 $D_s$;

longitudinal compression wave detection means connected to the sample to receive such waves therefrom; and measuring means connected to the wave generating means and the wave testing means and for testing the sample by measuring the propagation characteristics of the longitudinal compression waves through the sample.

36. Apparatus as claimed in claim 35, wherein the effective wavelength of the longitudinal compression waves is from 30 $D_s$ to 50 $D_s$.

37. Apparatus as claimed in claim 35, wherein the effective wavelength of the longitudinal compression waves is between 0.5 and 1 times the length of the sample to be employed with the apparatus.

38. Apparatus as claimed in claim 37, wherein the effective wavelength of the longitudinal compression waves is an integral fraction 2/X of the length of the sample where X is a whole number integer.

39. Apparatus as claimed in claim 35, wherein the effective wavelength of the longitudinal compression waves is at least approximately equal to rhw length of the sample to be employed with the apparatus.

40. Apparatus as claimed in claim 35, including
a furnace in which the sample to be tested can be enclosed; and means for controlling the furnace to cycle the sample through a period of increasing temperature, a subsequent period of high temperature, and a final period of decreasing temperature while the material of the sample is tested.

41. Apparatus for the non-destructive testing of materials using longitudinal compression waves and for use with a sample of the material having two parallel faces, the apparatus comprising:

a waveguide for the application to one of the sample parallel faces for the supply to the sample of longitudinal compression waves;

longitudinal compression wave generating means connected to the waveguide for supplying longitudinal compression waves thereto;

wherein the effective wavelength of the longitudinal compression waves is between 0.5 and 1 times the length of the sample to be employed with the apparatus;

longitudinal compression wave detection means connected to the sample to receive such waves therefrom; and measuring means connected to the wave generating means and the wave testing means and for testing the sample by measuring the propagation characteristics of the longitudinal compression waves through the sample.

42. Apparatus as claimed in claim 41, wherein the effective wavelength is an integral fraction 2/X of the length of the sample where X is a whole number integer.

43. Apparatus as claimed in claim 41, wherein the effective wavelength of the longitudinal compression waves is at least approximately equal to the length of the sample to be employed with the apparatus.

44. Apparatus as claimed in claim 41, including:

a furnace in which the sample to be tested can be enclosed; and means for controlling the furnace to cycle the sample through a period of increasing temperature, a subsequent period of high temperature, and a final period of decreasing temperature while the material of the sample is tested.

* * * * *